(12) United States Patent
Wels et al.

(10) Patent No.: US 8,530,637 B2
(45) Date of Patent: Sep. 10, 2013

(54) OPTIMIZED DNA SEQUENCE OF AN ANTIBODY TO IMPROVE QUALITY AND YIELD OF BACTERIALLY EXPRESSED ANTIBODY FUSION PROTEINS

(75) Inventors: Winfried S. Wels, Frankfurt am Main (DE); Benjamin Daelken, Frankfurt am Main (DE); Sylvia E. Schwarz, Frankfurt am Main (DE)

(73) Assignee: Chemotherapeutisches Forschungsinstitut Georg-Speyer-Haus, Frankfurt am Main (DE)

( * ) Notice: Subject to any disclaimer, the term of this patent is extended or adjusted under 35 U.S.C. 154(b) by 0 days.

(21) Appl. No.: 12/985,542

(22) Filed: Jan. 6, 2011

(65) Prior Publication Data

US 2011/0105742 A1    May 5, 2011

Related U.S. Application Data

(62) Division of application No. 12/170,623, filed on Jul. 10, 2008, now Pat. No. 7,887,801.

(60) Provisional application No. 60/949,580, filed on Jul. 13, 2007.

(51) Int. Cl.
*C07H 21/04* (2006.01)

(52) U.S. Cl.
USPC .......................................... 536/23.4

(58) Field of Classification Search
None
See application file for complete search history.

(56) References Cited

U.S. PATENT DOCUMENTS 6,498,233 B1 * 12/2002 Wels et al. .................... 530/350

OTHER PUBLICATIONS

Altenschmidt, U et al., *International Journal of Cancer*, vol. 73, No. 1, pp. 117-124 (Sep. 26, 1997).
Azemar et al., *Breast Cancer Research and Treatment*, NIJHOFF, Boston, US, vol. 82, pp. 155-164 (2003).
Beerli, RR et al., *Breast Cancer Research and Treatment*, NIJHOFF, Boston, US, vol. 38, pp. 11-17 (1996).
Messmer, D et al., *Breast Cancer Research*, vol. 7, No. 5, pp. 185-186 (2005).
Schmidt, M et al., *Gynecologic Oncology*, Academic Press, London, GB, vol. 80, No. 2, pp. 145-155 (Feb. 2001).
Von Minckwitz, G et al., *Breast Cancer Research*, vol. 7, No. 5, pp. R617-R626 (2005).
Wang, L et al., *Prostate*, Wiley-Liss, New York, NY, vol. 47, No. 1, pp. 21-28 (Apr. 1, 2001).
Wels, W et al., *Cancer Research*, vol. 52, No. 22, pp. 6310-6317 (Nov. 15, 1992).

* cited by examiner

*Primary Examiner* — Laura B Goddard
(74) *Attorney, Agent, or Firm* — Chalin A. Smith; Smith Patent Consulting (57) ABSTRACT

Object matter of the invention is an optimized DNA sequence encoding the scFv(FRP5) antibody fragment. This novel sequence prevents the generation of the undesired by-product in the context of an scFv(FRP5)-ETA fusion protein, and possibly also other bacterially expressed scFv(FRP5)-containing fusion proteins. The DNA sequence of the scFv (FRP5) domain of scFv(FRP5)-ETA was modified by exchanging a distinct codon, thereby preventing an otherwise possible internal start of protein translation.

23 Claims, 2 Drawing Sheets

OPTIMIZED DNA SEQUENCE OF AN ANTIBODY TO IMPROVE QUALITY AND YIELD OF BACTERIALLY EXPRESSED ANTIBODY FUSION PROTEINS

This application is a divisional of U.S. patent application Ser. No. 12/170,623, filed Jul. 10, 2008, which, in turn, claims the benefit of U.S. Provisional Application Ser. No. 60/949,580 filed Jul. 13, 2007, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Apr. 29, 2013, is named LNK_034D1_PatentINSL_April2013_ST25.txt and is 18,585 bytes in size.

The antibody-toxin scFv(FRP5)-ETA is a recombinant fusion protein composed of a single-chain antibody fragment derived from the ErbB2-specific antibody FRP5, via gene fusion linked to a truncated fragment of Pseudomonas exotoxin A. High and selective antitumoral activity of scFv(FRP5)-ETA against ErbB2 expressing cancer cells in vitro, in animal models and in cancer patients has been described in detail in the literature. Production of scFv(FRP5)-ETA by bacterial expression in E. coli using current methodology results, in addition to the major product of intact scFv(FRP5)-ETA, also in a truncated scFv(FRP5)-ETA fragment as a by-product. Complete elimination of this undesired fragment using classical protein purification techniques has so far not been achieved.

Object matter of the invention is an optimized DNA sequence encoding the scFv(FRP5) antibody fragment. This novel sequence prevents the generation of the undesired by-product in the context of an scFv(FRP5)-ETA fusion protein, and possibly also other bacterially expressed scFv(FRP5)-containing fusion proteins. The DNA sequence of the scFv(FRP5) domain of scFv(FRP5)-ETA was modified by exchanging a distinct codon, thereby preventing an otherwise possible internal start of protein translation.

BACKGROUND OF THE INVENTION

Epithelial cells of most organs typically express the ErbB2 (HER2) receptor tyrosine kinase at low levels. However, in several types of carcinomas, ErbB2 expression is strongly enhanced, often as a result of gene amplification. Due to this preferential expression in many tumors of epithelial origin, its accessibility from the extracellular space, and its involvement in the transformation process, the ErbB2 receptor tyrosine kinase is a preferred target for directed cancer therapy.

Based on a truncated Pseudomonas exotoxin A derivative lacking the toxin's endogenous cell binding domain, a recombinant toxin was developed that employs a single-chain Fv antibody fragment of the ErbB2-specific monoclonal antibody FRP5 for targeting of the toxin to ErbB2 (1). In in vitro cell killing experiments, this bacterially expressed scFv(FRP5)-ETA molecule displayed potent antitumoral activity against a wide range of established and primary human tumor cells, including breast and ovarian carcinomas (1-3), squamous cell carcinomas (4, 5) and prostate carcinomas (6). In experimental animals scFv(FRP5)-ETA effectively inhibited growth of established human tumor xenografts (1, 3-5) and murine and rat tumor cells stably transfected with human c-erbB2 constructs (7, 8). In cancer patients, intratumoral injection of scFv(FRP5)-ETA into cutaneous lesions of ErbB2 expressing tumors resulted in a response rate of 60%, with complete regression of injected tumor nodules observed in 40%, and partial reduction in the size of injected tumors in another 20% of patients (9). In a recent phase I clinical study, maximum tolerated dose (MTD), dose limiting toxicity and pharmacokinetic parameters of intravenously injected scFv(FRP5)-ETA were determined (10). Thereby three out of 18 patients showed stable disease, and in another three patients clinical signs of activity in terms of signs and symptoms were observed.

SUMMARY OF THE INVENTION

Preparations of therapeutic proteins for the treatment of human patients must meet very high standards of purity and homogeneity to qualify for approval by regulatory authorities. By-products contaminating preparations of the active compound may cause adverse events in a patient, such as toxic reactions, and/or the induction of undesired immune responses. Therefore, such by-products must be removed to the extent technically possible, and for any remaining by-products, possible biological activities or the absence thereof must be individually demonstrated. As a consequence, production costs will dramatically increase due to the requirement for sophisticated and expensive purification techniques used to remove such undesired by-products, and/or due to additional testing that is required if a particular by-product cannot be removed.

Figure 1:
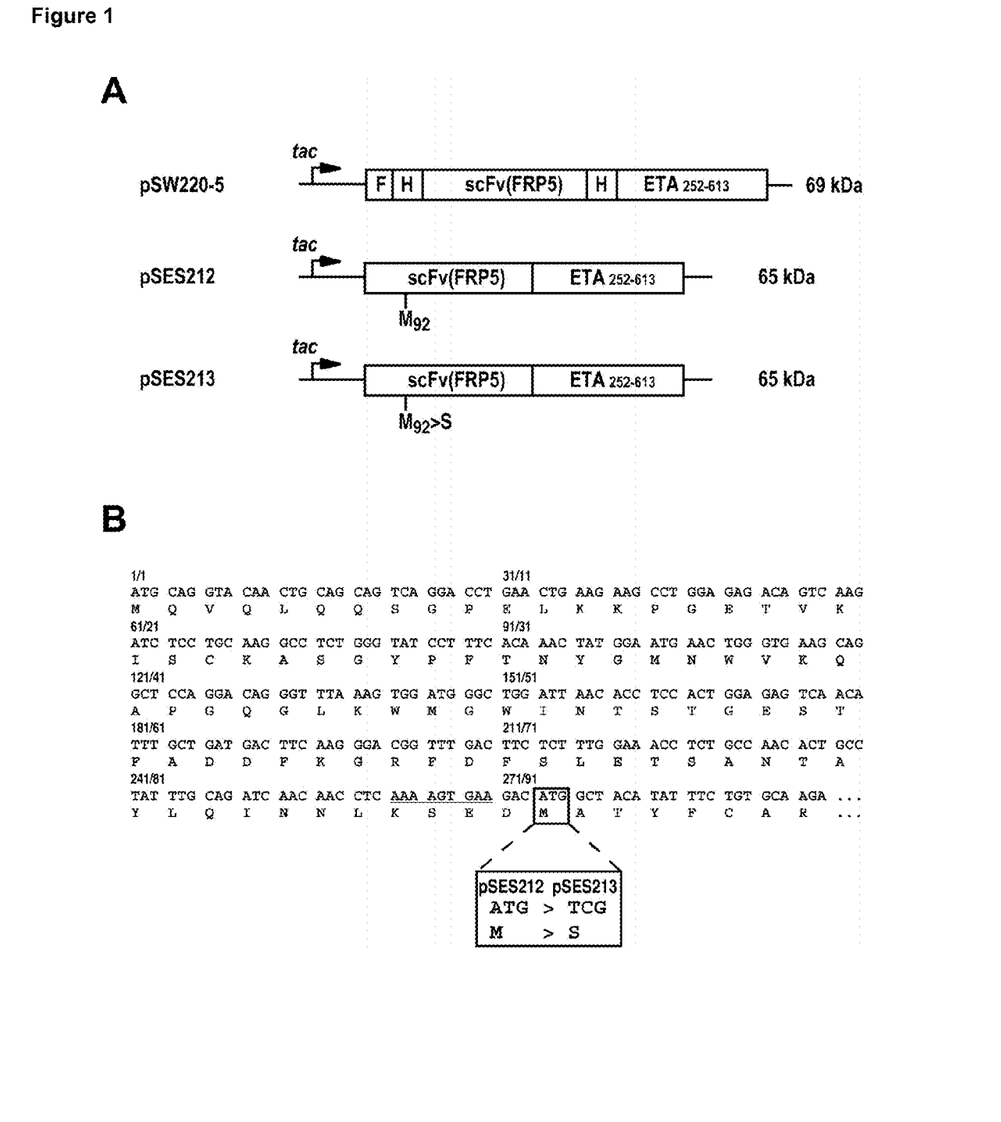
FIG. 1: Overview of variations of the antibody toxin scFv (FRP5)-ETA and specific sequence characteristics (A) Constructs for bacterial expression of scFv(FRP5)-ETA derivatives. All expression cassettes are under the control of the IPTG-inducible tac-promoter and code for the ErbB2-specific scFv(FRP5), fused to exotoxin A (ETA) of *Pseudomonas aeruginosa* (residues 252-613 of the wildtype toxin). Plasmid pSW220-5 carries sequences coding for an N-terminal FLAG tag (F) and two His$_6$ clusters (H). In pSES212 and pSES213, the FLAG tag and the His$_6$ clusters are deleted. pSES213 carries a mutation within the scFv(FRP5) sequence changing Methionine (M) at position 92 to Serine (S).

For production of the scFv(FRP5)-ETA antibody-toxin for in vivo applications, so far mainly the bacterial expression vector pSW220-5 was used (7). This plasmid encodes a fusion protein composed of the ErbB2-specific scFv antibody fragment scFv(FRP5) derived from monoclonal antibody FRP5 (11, 12), genetically fused to truncated Pseudomonas exotoxin A (ETA), representing amino acid residues 252-613 of the wildtype toxin. In addition, the scFv(FRP5)-ETA expression unit in plasmid pSW220-5 includes sequences for two hexahistidine clusters ($His_6$) and an N-terminal FLAG tag for purification and detection of the protein (FIG. 1A). Protein preparations from bacterial expression cultures transformed with pSW220-5 contain a major product corresponding to full-length scFv(FRP5)-ETA, and a major by-product (about 10%) that migrates directly below the main band. Both protein bands can be detected in purified protein preparations by Coomassie-staining of SDS-PAA gels (see FIG. 2A, left lane), and with ETA-specific antibodies in immunoblot experiments (data not shown). Also previous immunoblot experiments revealed that the by-product is being recognized by antibodies to the exotoxin A portion of scFv(FRP5)-ETA. This by-product has therefore been thought to be generated during or after expression by protein degradation of full-length scFv(FRP5)-ETA by bacterial proteases. Using standard protein purification techniques, it has not been possible so far to remove this truncated protein fragment.

DETAILED DESCRIPTION OF THE INVENTION AND OF EXEMPLARY EMBODIMENTS

It is an object of the invention to prevent the generation of this truncated fragment of scFv(FRP5)-ETA without affecting the therapeutically relevant biological activities of the full-length protein. Upon application of this invention, this undesired by-product can no longer form during bacterial expression. Therefore protein preparations of higher purity can now easily be produced.

This invention covers the modification of the expression unit encoding scFv(FRP5)-ETA in such a way, that a homogeneous protein preparation can be obtained from bacterial expression cultures, which lacks the truncated by-product mentioned above. In contrast to previous considerations, we hypothesized that the by-product may not be generated by proteolytic degradation of full-length protein, but may be the result of an alternative start of protein translation from an internal AUG codon within the scFv(FRP5) sequence of the scFv(FRP5)-ETA mRNA.

In a first aspect, the invention relates to a polypeptide comprising a first amino acid sequence which comprises amino acids 2-120 of SEQ ID NO:11, and a second amino acid sequence which comprises amino acids 136-242 of SEQ ID NO:11, wherein said first and second amino acid sequence are linked by a peptide spacer group. Preferably, the polypeptide of the invention comprises the following structure:

$$V_H\text{-Sp-}V_L,$$

wherein
$V_H$ is the first amino acid sequence,
Sp is the peptide spacer group, and
$V_L$ is the second amino acid sequence.

Accordingly, the first amino acid sequence is usually at the N-terminal end of the polypeptide. The polypeptide of the invention is usually a single-chain antibody wherein the heavy chain variable domain and the light chain variable domain are linked by way of a spacer group, preferably a peptide. The first amino acid sequence in the polypeptide of the invention represents the heavy chain variable domain, and the second amino acid sequence represents the light chain variable domain. Most preferred is a single-chain antibody wherein the heavy chain variable domain is located at the N-terminus of the recombinant antibody.

The first amino acid sequence comprises amino acids 2-120 of SEQ ID NO:11, preferably comprises amino acids 1-120 of SEQ ID NO:11, and more preferably consists of amino acids 1-120 of SEQ ID NO:11. In a more preferred embodiment, the first amino acid sequence comprises amino acids 2-120 of SEQ ID NO: 1, preferably comprises amino acids 1-120 of SEQ ID NO:1, and more preferably consists of amino acids 1-120 of SEQ ID NO:1.

The second amino acid sequence comprises amino acids 136-242 of SEQ ID NO:11, but preferably consists of amino acids 136-242 of SEQ ID NO:11.

The peptide spacer group may have a length of from 3 to 30 amino acids, preferably of from 5 to 25 amino acids, more preferably of from 10 to 20 amino acids, most preferably of about 15 amino acids (e.g. 13, 14, 15, 16 or 17 amino acids). It is also preferred that the peptide spacer group consists of amino acids selected from glycine and serine. Particularly preferred is an embodiment, wherein the spacer group is the 15 amino acid peptide consisting of three repetitive subunits of Gly-Gly-Gly-Gly-Ser (SEQ ID NO: 13).

The polypeptide of the invention preferably comprises the amino acid sequence as shown in SEQ ID NO:11, but more preferably comprises the amino acid sequence as shown in SEQ ID NO:1.

The amino acid Xaa in SEQ ID NO:11 may be any amino acid except methionine or be absent. In the latter case, the amino acids at positions 91 and 93 are linked directly to each other via a peptide bond. Xaa in SEQ ID NO:11 may be any amino acid except methionine, including naturally occurring amino acids, non-naturally occurring amino acids and modified amino acids. When Xaa is a naturally occurring amino acid, Xaa may be alanine, cysteine, aspartic acid, glutamic acid, phenylalanine, glycine, histidine, isoleucine, lysine, leucine, asparagine, proline, glutamine, arginine, serine, threonine, valine, tryptophane, tyrosine or selenocysteine. Preferably, Xaa is selected from the group consisting of serine, alanine, threonine and cysteine. Most preferably, Xaa is serine. When Xaa is a non-naturally occurring or modified amino acid, possible meanings of Xaa include, but are not limited to ornithine, norleucine, norvaline, hydroxyproline, hydroxylysine, ethylglycine and ethylasparagine. Xaa may also be any modified amino acid as defined in table 4 of WIPO Standard ST.25, which is incorporated herein by reference.

Alternatively, Xaa may be absent which means that the methionine at position 92 of the FRP5 sequence (see e.g. SEQ ID NO:9) has been deleted and is not replaced by another amino acid. According to that embodiment, the polypeptide of the invention may comprise the amino acid sequence as shown in SEQ ID NO:12.

The single-chain recombinant antibody may further comprise an effector molecule and/or signal sequences facilitating the processing of the antibody by the host cell in which it is prepared.

Effector molecules considered are those useful for therapeutic or diagnostic purposes, for example enzymes causing a detectable reaction, e.g. phosphatase, such as alkaline phosphatase from *E. coli* or mammalian alkaline phosphatase, e.g. bovine alkaline phosphatase, horseradish peroxidase, beta-D-galactosidase, glucose oxidase, glucoamylase, carbonic anhydrase, acetylcholinesterase, lysozyme, malate dehydrogenase or glucose-6-phosphate, a peptide having particular binding properties, e.g. streptavidin from *Streptomyces avidinii* strongly binding to biotin, or enzymes, toxins or other drugs attacking the cells to which the antibody is bound, e.g. a protease, a cytolysin or an exotoxin, for example ricin A, diphtheria toxin A, or *Pseudomonas* exotoxin. In the following a single-chain recombinant antibody further comprising an effector molecule is referred to as fusion protein or intended to be within the meaning of the terms "single chain (recombinant) antibody" or "recombinant antibody", if appropriate. The effector molecule may be a polypeptide having cell killing activity. Cell killing activity may be determined according to Example 3 of this application.

The term effector molecule also includes biologically active variants of the above-mentioned proteins, e.g. variants produced from a DNA which has been subjected to in vitro mutagenesis, with the provision that the protein encoded by said DNA retains the biological activity of the native protein. Such modifications include an addition, exchange or deletion of amino acids, the latter resulting in shortened variants. For example, an enzyme, such as phosphatase, may be prepared from a DNA which has been modified to facilitate the cloning of the encoding gene, or an exotoxin, such as *Pseudomonas* exotoxin, may be prepared from a DNA which has been mutated to delete the cell binding domain and/or to enhance or reduce its cell killing potential.

The effector polypeptide may comprise the amino acids 245-606 of SEQ ID NO:1.

The term effector molecule also includes chemical entities having cell killing activity. Cell killing activity may be determined according to Example 3 of this application. Such chemical entities include, but are not limited to, chemotherapeutic drugs, cytotoxic compounds and cytostatic compounds. Examples of chemotherapeutic drugs and cytotoxic compounds are
  alkylating agents
  cytotoxic antibiotics
  antimetabolites
  vinca alkaloids and etoposide
  others Alkylating agents react with nucleophilic residues, such as the chemical entities on the nucleotide precursors for DNA production. They affect the process of cell division by alkylating these nucleotides and preventing their assembly into DNA. Suitable alkylating agents include Mustargen, Estramustinphosphate, Melphalan, Chlorambucil, Prednimustin, Cyclophosphamide, Ifosfamid, Trofosfamid, Busulfan, Treosulfan, Thiotepa, Carmustin (BCNU), Lomustin (CCNU), Nimustin (ACNU), Dacarbazine (DTIC), Procarbazine, Cisplatin, and Carboplatin.

Cytotoxic antibiotics act by directly inhibiting DNA or RNA synthesis and are effective throughout the cell cycle. Suitable cytotoxic antibiotics include Actinomycin D, Daunorubicin, Doxorubicin, Epirubicin, Idarubicin, Mitoxantron, Bleomycin, Mitomycin C, Irinotecan (CPT-11), and Topotecan.

Antimetabolites interfere with cellular enzymes or natural metabolites that are involved in the process of cell division, thus disrupting the division of the cell. Suitable Antimetabolites include Methotrexate, 6-Mercaptopurine, 6-Thioguanine, Pentostatin, Fludarabinphosphate, Cladribine, 5-Fluorouracil, Capecitabine, Cytarabin, Gemcitabine, and Hydroxyurea.

Plant alkaloids and etoposides are agents derived from plants. They inhibit cell replication by preventing the assembly of the cell's components that are essential to cell division (e.g. Vinca alkaloids; Etoposide). Suitable alkaloids and etoposides include Vincristin, Vinblastin, Vindesin, Etoposide (VP16), Teniposide (VM26).

The group of compounds labeled 'Others' is made up primarily of taxanes (e.g. Paclitaxel, Taxol, Docetaxel, Taxotere) and metal complexes (e.g. cisPlatinum), and signal transduction inhibitors (STIs), inhibitors of specific enzyme functions, including but not limited to histone deacetylase inhibitors, kinase and protease inhibitors. The histone deacetylase (HDAC) inhibitor may be selected from the group consisting of vorinostat, belinostat, PCI-24781, CHR-3242, JNJ-16241199, MGCD-0103, romidepsin, MS-275, butyrate, valproic acid and combinations thereof. The kinase inhibitor may be selected from the group consisting of imatinib, cedaritinib, gefitinib, vandetanib, sarafenib, danatinib, lestaurtinib, enzastaurin, pazopanib, alvocidib, nilotinib, vatalinib, erlotinib, suninib and combinations thereof. The protease inhibitor may be selected from the group consisting of WX-UK1, bortezomib and combinations thereof.

Alternatively, the chemical entity having cell killing activity may be a radioactive substance, e.g. Cobalt-60.

The effector molecule may be bound to the polypeptide of the invention via a covalent bond or via a non-covalent linkage. When the effector molecule is bound to the polypeptide of the invention via a covalent bond it may be fused to the N-terminal or to the C-terminal part of the polypeptide. Preferably, the effector molecule is fused to the C-terminal end of the second amino acid sequence to form a fusion polypeptide. There may be one or more (e.g. two, three, four or five) amino acids between the second amino acid sequence and the amino acid sequence of the effector molecule in the fusion polypeptide.

Most preferably, the polypeptide of the invention comprises the amino acids 2-606 of the amino acid sequence SEQ ID NO:3, or it comprises the amino acids 1-606 of the amino acid sequence SEQ ID NO:3, or it consists of the amino acid sequence as shown in SEQ ID NO:3.

The polypeptide of the invention optionally comprises another peptide, e.g. a peptide facilitating purification, in particular a peptide being an epitope against which an antibody is available, such as the FLAG peptide. Purification, e.g. by means of affinity chromatography, of a fusion protein comprising such a peptide is advantageous e.g. in that it may be faster, more specific and/or gentler. The peptide may be placed at the N-terminus of the fusion protein, in between the recombinant antibody and the effector molecule, or at the C-terminus of the fusion protein. Preferably, it is located at the N-terminus or at the C-terminus, in particular at the N-terminus. Preferably, these constructs also contain a cleavage site, so that the fusion protein can be liberated therefrom, either by enzymatic cleavage, e.g. by enterokinase or by Factor Xa, or by the chemical methods known in the art. Furthermore these constructs may comprise a peptide spacer consisting of one or more, e.g. 1 to 10, in particular about 2 amino acids, said spacer facilitating the linkage of the above-mentioned peptide and/or the cleavage site to the recombinant antibody. The cleavage site is placed in such a way that the fusion protein comprising the recombinant antibody and the effector molecule can be easily liberated, if desired, preferably in vitro. For example, in a protein construct comprising the fusion protein designated scFv(FRP5)-ETA, the FLAG peptide and an enterokinase cleavage site are linked to a spacer and placed in front of the Fv heavy chain/light chain variable domain and exotoxin A fusion protein. If desired, the FLAG peptide can be cleaved off by enterokinase, preferably after affinity purification of the protein, yielding a fusion protein comprising the single-chain antibody Fv(FRP5) and exotoxin A.

Another aspect of this invention is a polynucleotide encoding the polypeptide of the invention. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

Preferred are polynucleotides encoding the amino acid sequence as shown in SEQ ID NO:11. More preferably, the polynucleotide encodes a polypeptide comprising the amino acid sequence as shown in SEQ ID NO:1. Even more preferably, the polynucleotide encodes a polypeptide comprising the amino acid sequence as shown in SEQ ID NO: 3. The most preferred polynucleotides comprise the nucleotide sequence as shown in SEQ ID NO:2 or the nucleotide sequence as shown in SEQ ID NO:4.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid of a vector containing a polynucleotide according to the present invention. The terms "plasmid" and "vector" refer to an extrachromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Usually, the polynucleotide in the plasmid or vector is operably linked to one or more expression control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation. A "promoter" is a DNA sequence upstream from the start of transcription of a gene and involved in recognition and binding of RNA polymerase and/or other proteins to initiate transcription of the gene. Usually, the promoter determines under what conditions the gene is expressed. Usually, the promoter used herein is heterologous to the polynucleotide of the invention to which it is operably linked.

Vectors typically perform two functions in collaboration with compatible host cells. One function is to facilitate the cloning of the nucleic acid that encodes the immunoglobulin variable domains, i.e. to produce usable quantities of the nucleic acid (cloning vectors). The other function is to provide for replication and expression of the recombinant gene constructs in a suitable host, either by maintenance as an extrachromosomal element or by integration into the host chromosome (expression vectors). A cloning vector comprises the recombinant gene constructs as described above, an origin of replication or an autonomously replicating sequence, dominant marker sequences and, optionally, signal sequences and additional restriction sites. An expression vector additionally comprises expression control sequences essential for the transcription and translation of the recombinant genes.

An origin of replication or an autonomously replicating sequence is provided either by construction of the vector to include an exogeneous origin such as derived from Simian virus 40 (SV 40) or another viral source, or by the host cell chromosomal mechanisms.

The markers allow for selection of host cells which contain the vector. Selection markers include genes which confer resistance to heavy metals such as copper or to antibiotics such as geneticin (G-418), kanamycin or hygromycin, or genes which complement a genetic lesion of the host cell such as the absence of thymidin kinase, hypoxanthine phosphoryl transferase, dihydrofolate reductase or the like.

Signal sequences may be, for example, presequences or secretory leaders directing the secretion of the recombinant antibody, splice signals, or the like. Examples for signal sequences directing the secretion of the recombinant antibody are sequences derived from the ompA gene, the pelB (pectate lyase) gene or the phoA gene.

As expression control sequences, the vector DNA comprises a promoter, sequences necessary for the initiation and termination of transcription and for stabilizing the mRNA and, optionally, enhancers and further regulatory sequences.

A wide variety of promoting sequences may be employed, depending on the nature of the host cell. Promoters that are strong and at the same time well regulated are the most useful.

Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of viral origin, e.g. derived from Simian virus, polyoma virus, bovine papilloma virus or Moloney sarcoma virus, or of genomic, especially murine, origin.

Examples of vectors which are suitable for replication and expression in an *E. coli* strain are bacteriophages, for example derivatives of lambda bacteriophages, or plasmids, such as, in particular, the plasmid ColE1 and its derivatives, for example pMB9, pSF2124, pBR317 or pBR322 and plasmids derived from pBR322, such as pUC9, pUCK0, pHR1148 and pLc24. Suitable vectors contain a complete replicon, a marker gene, recognition sequences for restriction endonucleases, so that the foreign DNA and, if appropriate, the expression control sequence can be inserted at these sites, and optionally signal sequences and enhancers.

Microbial promoters are, for example, the strong leftward promoter PL of bacteriophage lambda which is controlled by a temperature sensitive repressor. Also suitable are *E. coli* promoters such as the lac (lactose) promoter regulated by the lac repressor and induced by isopropyl-beta-D-thiogalactoside, the trp (tryptophan) promoter regulated by the trp repressor and induced e.g. by tryptophan starvation, and the tac (hybrid trp-lac promoter) regulated by the lac repressor.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the 2μ (2 mikron) plasmid DNA from *Saccharomyces cerevisiae* can be used. Such vectors will get integrated by recombination into 2μ plasmids already existing within the cell, or replicate autonomously. 2μ sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Vectors suitable for replication and expression in mammalian cells are preferably provided with promoting sequences derived from DNA of viral origin, e.g. from Simian virus 40 (SV40), Rous sarcoma virus (RSV), adenovirus 2, bovine papilloma virus (BPV), papovavirus BK mutant (BKV), or mouse or human cytomegalovirus (CMV). Alternatively, the vectors may comprise promoters from mammalian expression products, such as actin, collagen, myosin etc., or the native promoter and control sequences which are normally associated with the desired gene sequence, i.e. the immunoglobulin H-chain or L-chain promoter.

Preferred vectors are suitable for both procaryotic and eucaryotic hosts and are based on viral replication systems. Particularly preferred are vectors comprising Simian virus promoters, e.g. pSVgpt or pSVneo, further comprising an enhancer, e.g. an enhancer normally associated with the immunoglobulin gene sequences, in particular the mouse Ig H- or L-chain enhancer.

The recombinant DNA coding for a recombinant antibody of the invention can be prepared, for example, by culturing a transformed host cell and optionally isolating the prepared DNA.

Another aspect of the invention are host cells that are transformed with and/or contain the plasmid or the vector according to the present invention. Suitable host cells include prokaryotic and eukaryotic cells (e.g. mammalian cells), yeast cells, bacterial cells (e.g. E. coli cells). Preferred host cells are E. coli cells. Suitable host cells and transformation procedures are described in U.S. Pat. No. 5,939,531 and are incorporated herein entirely by reference.

The present invention also relates to methods of culturing the host cells and to methods for the preparation of the polypeptide of the invention. One aspect of the invention is a process for the preparation of the polypeptide of the invention, comprising culturing a host cell described herein under suitable conditions and recovering the polypeptide. Described in U.S. Pat. No. 5,939,531 are methods of culturing host cells and methods for producing recombinant single-chain antibody fragments and antibodies. These methods are applicable to the host cells of the present invention and to the polypeptides of the present invention mutatis mutandis and are incorporated herein in their entirety by reference.

Another aspect of the invention is the use of a polypeptide according to the invention or of a polynucleotide according to the invention for the manufacture of a medicament for the treatment of a disorder involving aberrant activity and/or expression of ErbB2 (e.g. cancer, tumors). Such disorders include, but are not limited to, breast cancer, prostate cancer, ovarian cancer, squamous cell carcinoma, head and neck cancer, non small cell lung cancer, pancreas cancer, gastric cancer, salivary gland cancer, parotid tumors, melanoma, cervical carcinoma, pancreas cancer, colon and colorectal cancer, bladder cancer, medulloblastoma, kidney cancer, liver cancer and stomach cancer. The disorder may also be metastasis and/or minimal residual disease.

The invention therefore also concerns pharmaceutical compositions (e.g. for treating tumors over-expressing the growth factor receptor c-erbB-2) comprising a therapeutically effective amount of a polypeptide according to the invention and a pharmaceutically acceptable carrier, diluent or vehicle. Preferred are pharmaceutical compositions for parenteral application. Compositions for intramuscular, subcutaneous or intravenous application are e.g. isotonic aqueous solutions or suspensions, optionally prepared shortly before use from lyophilized or concentrated preparations. Suspensions in oil contain as oily component the vegetable, synthetic or semi-synthetic oils customary for injection purposes. The pharmaceutical compositions may be sterilized and contain adjuncts, e.g. for conserving, stabilizing, wetting, emulsifying or solubilizing the ingredients, salts for the regulation of the osmotic pressure, buffer and/or compounds regulating the viscosity, e.g. sodium carboxycellulose, carboxymethylcellulose, sodium carboxymethylcellulose, dextran, polyvinylpyrrolidine or gelatine.

The pharmaceutical compositions of the invention contain from approximately 0.001% to approximately 50% of active ingredients. They may be in dosage unit form, such as ready-to-use ampoules or vials, or also in lyophilized solid form.

In general, the therapeutically effective dose for mammals is between approximately 0.1 and 100 μg of a polypeptide of the invention per kg body weight, more preferably between 1 and 50 μg, and even more preferably between 5 and 25 μg, depending on the type of polypeptide, the status of the patient and the mode of application. The specific mode of administration and the appropriate dosage will be selected by the attending physician taking into account the particulars of the patient, the state of the disease, the type of tumor treated, and the like. The pharmaceutical compositions of the invention are prepared by methods known in the art, e.g. by conventional mixing, dissolving, confectioning or lyophilizing processes. Pharmaceutical compositions for injection are processed, filled into ampoules or vials, and sealed under aseptic conditions according to methods known in the art.

In one embodiment, the polypeptide is administered in combination with another anti-cancer therapy. Incorporated herein are all anti-cancer therapies designated as "second therapeutic agent" in the WO 03/024442 A2.

In yet another aspect, the invention concerns a method for improving the production of a single-chain recombinant antibody directed to the extracellular domain of the receptor tyrosine kinase ErbB2, comprising preventing the initiation of translation from codon No. 92 of SEQ ID NO:9. This may be accomplished by modifying one or more nucleotides at positions 262-270 of SEQ ID NO:10 such that internal translation starting at codon No. 92 (Met 92) no longer occurs. The nucleotides may be substituted without changing the encoded amino acid sequence.

Three non-limiting examples of the nucleotide sequence of positions 262-270 are indicated in the following:

| | nucleotide position | | | | | | | | |
|---|---|---|---|---|---|---|---|---|---|
| | 262 | 263 | 264 | 265 | 266 | 267 | 268 | 269 | 270 |
| (1) | A | A | A | A | G | T | G | A | A |
| (2) | A | A | A | T | C | T | G | A | A |
| (3) | A | A | A | T | C | C | G | A | A |

Alternatively, these amino acid residues Lys, Ser or Glu may be replaced by other chemically similar or unrelated amino acids, naturally occurring or artificially generated, and may be encoded by nucleotides which are chemically modified.

Another possibility is (as described hereinabove) replacing M92 in the amino acid sequence SEQ ID NO:9 with a different amino acid. Preferably, the different amino acid is serine. Yet another possibility is (as described hereinabove) deleting M92 in the amino acid sequence SEQ ID NO:9 without replacing it by a different amino acid. This embodiment is represented by the amino acid sequence as shown in SEQ ID NO:12.

FIGURES

Otherwise pSES213 is identical to pSES212. (B) Representation of partial scFv(FRP5)-ETA DNA (SEQ ID NO:10) and protein sequences (SEQ ID NO:9) in plasmids pSES212 and pSES213. The change of a potential internal start-codon at codon position 92 from ATG to TCG is indicated. A sequence with moderate similarity to a Shine-Algernon sequence is underlined.

FIG. 2: Expression and biological antitumoral activity of variations of the antibody toxin scFv(FRP5)-ETA (A) SDS-PAGE analysis of scFv(FRP5)-ETA (220-5), scFv(FRP5)-ETA (212) and scFv(FRP5-M92S)-ETA (213) protein preparations. These scFv(FRP5)-ETA derivatives were expressed in E. coli DH5α transformed with the expression plasmids pSW220-5, pSES212 or pSES213. Inclusion bodies were isolated, denatured and renatured. Protein samples were separated by SDS-PAGE, and proteins were detected by Coomassie-staining. Bands corresponding to the full-length scFv (FRP5)-ETA and scFv(FRP5-M92S)-ETA proteins are indicated (open arrow). Major degradation products are present in samples expressed from plasmids pSW220-5 and pSES212 (closed arrow). In the scFv(FRP5-M92S)-ETA (213) preparation this undesired by-product is absent. (B) Biological activities of scFv(FRP5)-ETA (220-5) and scFv(FRP5-M92S)-ETA (213). Murine Renca-lacZ/ErbB2 renal carcinoma cells stably transfected with human c-erbB2 cDNA (left panel) and ErbB2-negative Renca-lacZ control cells (right panel) were incubated for 48 h with scFv(FRP5)-ETA (220-5) or scFv(FRP5-M92S)-ETA (213) in triplicate samples at the indicated concentrations. Viability of surviving cells was determined by measuring the absorbance at 590 nm in an MTT metabolization assay. Cells treated with PBS were used as a control. Error bars indicate standard deviation of the mean. (C) Activity of scFv(FRP5-M92S)-ETA (213) relative to the activity of scFv (FRP5)-ETA (220-5). The ratios for scFv(FRP5-M92S)-ETA (213) to scFv(FRP5)-ETA (220-5) of the $A_{590}$ values measured in (B) for antigen-positive and antigen-negative target cells at the indicated protein concentrations are given.

EXAMPLES

Example 1

Molecular Cloning of Modified Expression Constructs

Method

Construction of scFv(FRP5)-ETA Expression Vectors

The plasmid pSW220-5 was described before (7). It contains sequences coding for an N-terminal FLAG tag, a first $His_6$ cluster, the ErbB2-specific scFv(FRP5), a second $His_6$ cluster, and truncated Pseudomonas exotoxin A (residues 252-613 of the wildtype toxin) in a single open reading frame. Plasmid pSES211 (unpublished; provided by TopoTarget Germany AG) contains an open reading frame for scFv (FRP5)-ETA originally derived from pSW220-5 and still including the first N-terminal $His_6$ cluster, but lacking the N-terminal FLAG tag and the internal $His_6$ cluster between scFv(FRP5) and exotoxin A sequences. Plasmid pSES212 was derived by deleting the remaining N-terminal $His_6$ cluster of pSES211. The plasmid was generated by PCR using the oligonucleotide primers 5'NdeI-scFv(FRP5) 5'-CGATTAG-CATATGCAGGTACAACTG-CAGCAGTCAGGACC-3' (SEQ ID NO:5) and 3'XbaI-scFv(FRP5) 5'-GCTGCCGC-CCTCTAG-AGCTTTGATCTC-3' (SEQ ID NO:6) (BioSpring, Frankfurt, Germany) and plasmid pSES211 as a template. In this reaction, the sequence of the scFv(FRP5) fragment was amplified without the coding sequences for the N-terminal $His_6$ cluster. The PCR product was subcloned into the vector pCR2.1 by TA-cloning (Invitrogen, Karlsruhe, Germany). The resulting plasmid was digested with NdeI and XhoI, and the resulting scFv(FRP5) fragment was inserted into pSES211 digested with the same enzymes, yielding plasmid pSES212. The $Met_{92}$ to Ser mutation was introduced into plasmid pSES212 by site-directed mutagenesis via PCR using the oligonucleotide primers pSES212_M92S_sense 5'-CCTCAAAAGTGAAGACTCGGCTACATAT-TTCT-GTGC-3' (SEQ ID NO:7) and pSES212_M92S_as 5'-GCA-CAGAAATATGTAGCCGA-GTCTTCACTTTTGAGG-3' (SEQ ID NO:8) (BioSpring) and plasmid pSES212 as a template, yielding plasmid pSES213. The DNA sequences of all expression vectors were verified by DNA-sequencing.

Results

Figure 2:
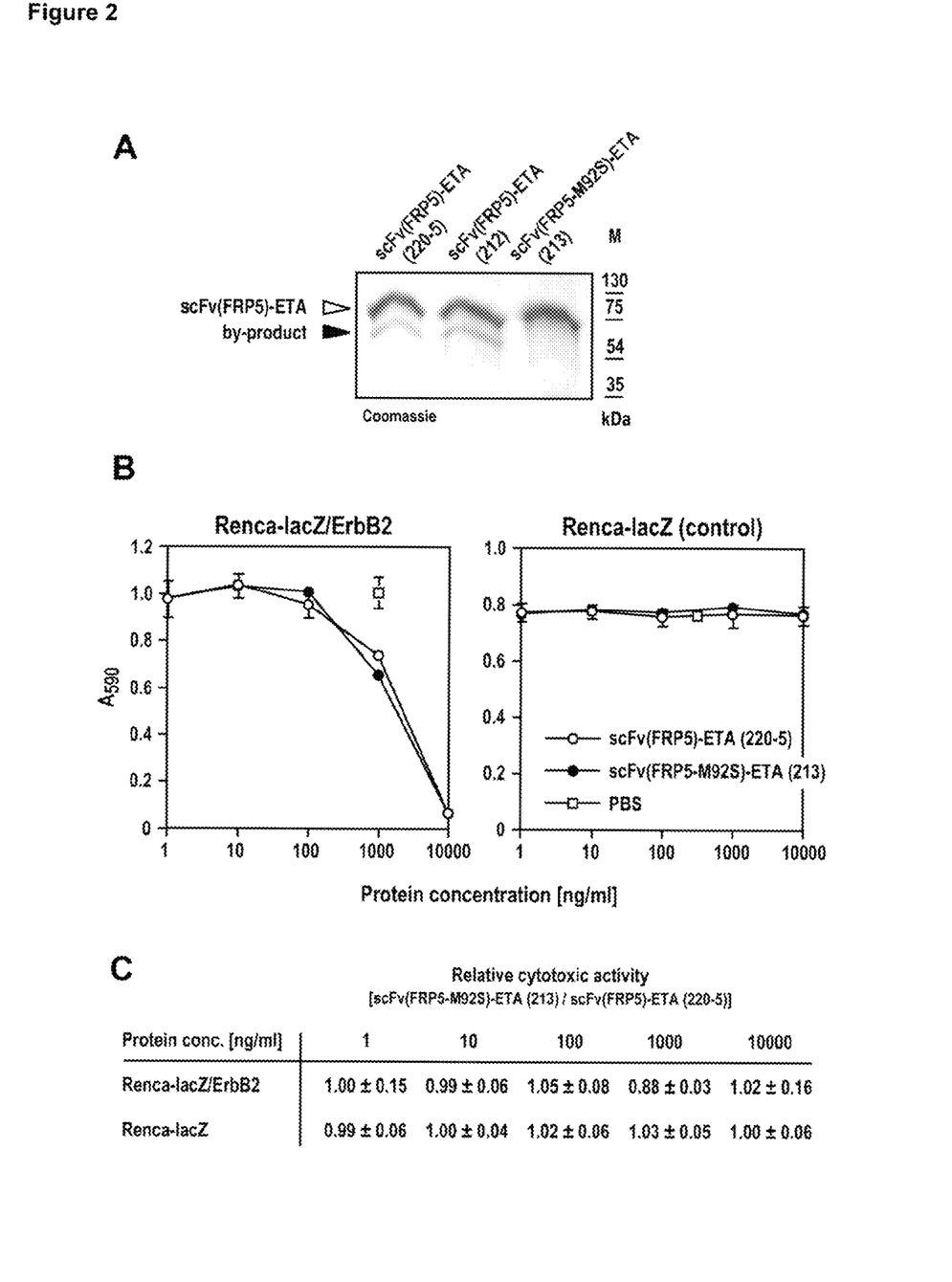

As a basis for the modification of the scFv(FRP5)-ETA coding region, we used the expression plasmid pSES212 (unpublished). The scFv(FRP5)-ETA coding region within pSES212 lacks the sequences encoding the N-terminal FLAG tag and the two $His_6$ clusters present in the corresponding region of pSW220-5 (see FIG. 1A). In addition, the vector backbone outside the scFv(FRP5)-ETA sequence of pSES212 is different from that of pSW220-5. These differences are not relevant in the context of this invention. As shown in FIG. 2A (left and middle lane), the truncated scFv (FRP5)-ETA by-product is being produced to the same extent by expression using pSES212 or pSW220-5 expression vectors. By sequence analysis, we identified an internal ATG codon (a potential internal AUG start codon on the mRNA level) within the scFv(FRP5) antibody heavy chain framework 3 region near the complementarity determining region 3 (CDR3) at nucleotide (nt) positions 274-276 of the open reading frame, corresponding to codon 92 of scFv(FRP5)-ETA in pSES212 (see FIG. 1B). This potential start codon is also preceded by a sequence with moderate similarity to a Shine-Dalgarno sequence at nt positions 262-270 (FIG. 1B; underlined).

To test whether modification of this internal ATG/AUG codon can prevent production of the undesired by-product, we generated the modified expression plasmid pSES213. pSES213 carries a mutation changing ATG at codon position 92 to TCG, which results in Serine (Ser; S) instead of Methionine (Met; M) as the amino acid residue encoded by this codon (see FIG. 1). pSES213 is otherwise identical to pSES212. Serine was chosen for replacement of Methionine, because it is present at the equivalent position in other murine antibody heavy chains of subgroup V (13). In addition, Ser and Met have similar isoelectric points, and a similar length of their side-chains.

In another embodiment of the invention, changing codon 92 in such a way that any amino acid other than Met is being encoded, or deleting codon 92, and/or mutating the sequence from nt 262-270 in such a way that it no longer displays similarity to a Shine-Dalgarno sequence, or does no longer act as a Shine-Dalgarno sequence, may solve the problem in a similar fashion.

Example 2

Expression of scFv(FRP5)-ETA Derivatives in *E. coli*

Method

Expression of scFv(FRP5)-ETA Derivatives in *E. coli*, Preparation of Inclusion Bodies, Solubilization and Refolding

*E. coli* DH5α were transformed with the expression plasmids pSW220-5, pSES212 or pSES213. One liter expression cultures (LB, 0.5% glucose, 50 µg/ml kanamycin in the case of pSES212 or pSES213, or 100 µg/ml ampicillin in the case of pSW220-5) were grown at 37° C. to an $OD_{600}$ of 0.8. The cultures were induced by addition of 0.5 mM IPTG for 3 hours. Cells were harvested by centrifugation (7500 g, 10 min), resuspended in PBS, and lysed in a French pressure cell. Inclusion bodies were collected by centrifugation (10000 g, 10 min, 4° C.) and washed by resuspension in washing buffer (2 M urea, 2% Triton X-100, 500 mM NaCl in PBS, pH 8) and subsequent centrifugation (10000 g, 10 min, 4° C.). Purified inclusion bodies were resuspended in solubilization buffer (8 M urea, 500 mM NaCl in PBS, pH 8). After centrifugation, the supernatant fractions were dialyzed against PBS, pH 7.4. Precipitates were removed by centrifugation (40000 g, 30 min, 4° C.) and subsequent filtration through a 0.22 µm filter. Proteins were stored in aliquots at −80° C.

Results

For production of scFv(FRP5)-ETA derivatives, *E. coli* DH5α were transformed with pSW220-5, pSES212 and pSES213, and selected on $LB_{Kan}$ (for pSES212 and pSES213) or $LB_{AMP}$ agar plates (for pSW220-5). Expression cultures of 1 l volume were inoculated with single colonies, and cultivated and induced as described in the Materials and Methods section below. Cell pellets of these cultures were resuspended in PBS, and lysed in a French pressure cell. scFv(FRP5)-ETA proteins were mainly present in the insoluble fractions of these lysates (data not shown). Inclusion bodies were collected by centrifugation and washed with buffer containing 2 M urea and 2% Triton X-100, before their denaturation with buffer containing 8 M urea. After centrifugation, the supernatant fractions were renatured by dialysis against PBS, and the partially purified renatured proteins were analyzed by SDS-PAGE and subsequent Coomassie-staining (see FIG. 2A). Proteins are indicated as scFv(FRP5)-ETA or scFv(FRP5-M92S)-ETA, followed by the name of the expression vector in brackets [scFv(FRP5)-ETA (220-5), scFv(FRP5)-ETA (212), scFv(FRP5-M92S)-ETA (213)]. For each expression culture, comparable yields of about 30-50 mg of renatured soluble protein were obtained. As shown in FIG. 2A, the scFv(FRP5)-ETA (220-5) and scFv(FRP5)-ETA (212) protein preparations obtained contain a major by-product (filled arrow), migrating in SDS-PAGE directly below the band of the full-length product (open arrow). In contrast, the scFv(FRP5-M92S)-ETA (213) preparation isolated following the very same protocol did not contain this undesired by-product.

These data demonstrate that exchange of codon 92 from ATG to TCG, and the corresponding amino acid residue from Methionine to Serine is surprisingly necessary and sufficient to completely prevent generation of the by-product.

Example 3

Biological Activity of scFv(FRP5-M92S)-ETA

Method

Cells and Culture Conditions

Murine renal carcinoma cells stably expressing *E. coli* β-galactosidase (Renca-lacZ), or β-galactosidase and human ErbB2 (Renca-lacZ/ErbB2) (8) were maintained in RPMI 1640 medium supplemented with 10% heat-inactivated FBS, 2 mM glutamine, 100 units/ml penicillin, 100 µg/ml streptomycin, 0.25 mg/ml Zeocin (Invitrogen, Karlsruhe, Germany), and 0.48 mg/ml G418 (Renca-lacZ/ErbB2).

Cell Viability Assay

Cells were seeded in 96-well plates at a density of $1.5 \times 10^4$ cells/well in normal growth medium. Different concentrations of scFv(FRP5)-ETA fusion proteins or diluent were added to triplicate samples, and the cells were incubated for 48 h at 37° C. in 5% $CO_2$ and 95% humidified air. An aliquot of 10 µl of 10 mg/ml MTT (3-(4,5-dimethylthiazole-2-yl)-2,5-diphenyltetrazolium bromide) (Sigma, Deisenhofen, Germany) in PBS was added to each well, and the cells were incubated for another 3 h. Cells were lysed by the addition of 90 µl of 20% SDS in 50% dimethyl formamide, pH 4.7. After solubilization, color development due to formation of the brown formazan metabolite was quantified by determining the absorbance at 590 nm in a microplate reader. Samples without cells served as blank.

Results

Selectivity and efficiency of tumor cell killing by scFv(FRP5)-ETA derivatives was evaluated in MTT metabolisation assays using murine Renca-lacZ/ErbB2 renal carcinoma cells expressing human ErbB2, and ErbB2-negative Renca-lacZ cells as a control (8). scFv(FRP5)-ETA (220-5) protein expressed and purified in parallel with scFv(FRP5-M92S)-ETA (213) protein was used as a standard for assaying cytotoxic activities. Target cells were incubated with increasing concentrations of the fusion proteins for 48 h. After cell lysis and solubilization, cell viability was quantified by determining the absorbance at 590 nm in a microplate reader (FIG. 2B). Samples without cells served as blank. At the tested concentrations of up to 10 µg/ml, scFv(FRP5)-ETA and scFv(FRP5-M92S)-ETA fusion proteins had no effect on the survival of ErbB2-negative Renca-lacZ cells (FIG. 2B). In contrast, scFv(FRP5)-ETA and scFv(FRP5-M92S)-ETA fusion proteins killed ErbB2-positive Renca-lacZ/ErbB2 cells equally well and in a concentration dependent manner (FIG. 2B). FIG. 2C represents the activity of scFv(FRP5-M92S)-ETA relative to that of scFv(FRP5)-ETA at the different concentrations tested. A value close to 1.00 indicates that there is no significant difference. The values obtained demonstrate that scFv(FRP5-M92S)-ETA is not significantly different in its biological activities from scFv(FRP5)-ETA.

These data demonstrate that exchange of codon 92 from ATG to TCG, and the corresponding amino acid residue from Methionine to Serine does surprisingly not affect the biological activities of scFv(FRP5)-ETA. The antitumoral activity of scFv(FRP5-M92S)-ETA is indistinguishable from that of scFv(FRP5)-ETA. The selectivity for ErbB2 expressing tumor cells is also retained.

The various embodiments of this invention described herein can be combined with each other.

REFERENCES

1. Wels W, Harwerth I M, Mueller M, Groner B, Hynes N E. Selective inhibition of tumor cell growth by a recombinant single-chain antibody-toxin specific for the erbB-2 receptor. Cancer Res 1992; 52:6310-7.
2. Spyridonidis A, Schmidt M, Bernhardt W, et al. Purging of mammary carcinoma cells during ex vivo culture of CD34+ hematopoietic progenitor cells with recombinant immunotoxins. Blood 1998; 91:1820-7.
3. Schmidt M, McWatters A, White R A, et al. Synergistic interaction between an anti-p185HER-2 *Pseudomonas*

4. Wels W, Beerli R, Hellmann P, et al. EGF receptor and p185erbB-2-specific single-chain antibody toxins differ in their cell-killing activity on tumor cells expressing both receptor proteins. Int J Cancer 1995; 60:137-44.
5. Azemar M, Schmidt M, Arlt F, et al. Recombinant antibody toxins specific for ErbB2 and EGF receptor inhibit the in vitro growth of human head and neck cancer cells and cause rapid tumor regression in vivo. Int J Cancer 2000; 86:269-75.
6. Wang L, Liu B, Schmidt M, Lu Y, Wels W, Fan Z. Antitumor effect of an HER2-specific antibody-toxin fusion protein on human prostate cancer cells. Prostate 2001; 47:21-8.
7. Altenschmidt U, Schmidt M, Groner B, Wels W. Targeted therapy of schwannoma cells in immunocompetent rats with an erbB2-specific antibody-toxin. Int J Cancer 1997; 73:117-24.
8. Maurer-Gebhard M, Schmidt M, Azemar M, et al. Systemic treatment with a recombinant erbB-2 receptor-specific tumor toxin efficiently reduces pulmonary metastases in mice injected with genetically modified carcinoma cells. Cancer Res 1998; 58:2661-6.
9. Azemar M, Djahansouzi S, Jäger E, et al. Regression of cutaneous tumor lesions in patients intratumorally injected with a recombinant single-chain antibody-toxin targeted to ErbB2/HER2. Breast Cancer Res Treat 2003; 82:155-64.
10. von Minckwitz G, Harder S, Hövelmann S, et al. Phase I clinical study of the recombinant antibody-toxin scFv (FRP5)-ETA specific for the ErbB2/HER2 receptor in patients with advanced solid malignomas. Breast Cancer Res 2005; 7:R617-R26.
11. Wels W, Harwerth I M, Zwickl M, Hardman N, Groner B, Hynes N E. Construction, bacterial expression and characterization of a bifunctional single-chain antibody-phosphatase fusion protein targeted to the human erbB-2 receptor. Biotechnology (N Y) 1992; 10:1128-32.
12. Harwerth I M, Wels W, Marte B M, Hynes N E. Monoclonal antibodies against the extracellular domain of the erbB-2 receptor function as partial ligand agonists. J Biol Chem 1992; 267:15160-7.
13. Kabat E A, Wu T T, Perry H M, Gottesman K S, Foeller C Sequences of proteins of immunological interest, 5 edition, Vol. 1. Washington: U.S. Department of Health and Human Services, 1991.

Sequences

```
Amino acid sequence of the optimized scFv(FRP5) antibody fragment
 S     The amino acid position 92 which has been optimised from
       a Methionine residue to a Serine residue is boxed
Underlined: Linker (aa 121-135)
                                                        SEQ ID NO: 1
  1 MQVQLQQSGPELKKPGETVKISCKASGYPFTNYGMNWVKQAPGQGLKWMG

51 WINTSTGESTFADDFKGRFDFSLETSANTAYLQINNLKSEDSATYFCARW

101 EVYHGYVPYWGQGTTVTVSSGGGGSGGGGSGGGGSDIQLTQSHKFLSTSV

151 GDRVSITCKASQDVYNAVAWYQQKPGQSPKLLIYSASSRYTGVPSRFTGS

201 GSGPDFTFTISSVQAEDLAVYFCQQHFRTPFTFGSGTKLEIK

Nucleotide sequence encoding the optimized scFv(FRP5)
antibody fragment;
 TCG   The nucleotides encoding the optimised amino acid
       position 92, here encoding the amino acid Serine is boxed
                                                        SEQ ID NO: 2
  1 ATGCAGGTACAACTGCAGCAGTCAGGACCTGAACTGAAGAAGCCTGGAGA

51 GACAGTCAAGATCTCCTGCAAGGCCTCTGGGTATCCTTTCACAAACTATG

101 GAATGAACTGGGTGAAGCAGGCTCCAGGACAGGGTTTAAAGTGGATGGGC

151 TGGATTAACACCTCCACTGGAGAGTCAACATTTGCTGATGACTTCAAGGG

201 ACGGTTTGACTTCTCTTTGGAAACCTCTGCCAACACTGCCTATTTGCAGA

251 TCAACAACCTCAAAAGTGAAGACTCGGCTACATATTTCTGTGCAAGATGG

301 GAGGTTTACCACGGCTACGTTCCTTACTGGGGCCAAGGGACCACGGTCAC

351 CGTTTCCTCTGGCGGTGGCGGTTCTGGTGGCGGTGGCTCCGGCGGTGGCG

401 GTTCTGACATCCAGCTGACCCAGTCTCACAAATTCCTGTCCACTTCAGTA

451 GGAGACAGGGTCAGCATCACCTGCAAGGCCAGTCAGGATGTGTATAATGC

501 TGTTGCCTGGTATCAACAGAAACCAGGACAATCTCCTAAACTTCTGATTT

551 ACTCGGCATCCTCCCGGTACACTGGAGTCCCTTCTCGCTTCACTGGCAGT

601 GGCTCTGGGCCGGATTTCACTTTCACCATCAGCAGTGTGCAGGCTGAAGA

651 CCTGGCAGTTTATTTCTGTCAGCAACATTTTCGTACTCCATTCACGTTCG

701 GCTCGGGGACAAAATTGGAGATCAAA
```

-continued

Amino acid sequence of scFv(FRP5)-ETA (213)
[S]   The amino acid position 92 which has been optimised
      from a Methionine residue to a Serine residue is boxed
Bold Antibody domain (aa 2-242)
Underligned, Linker (aa 121-135)
Italics ETA domain (aa 245-606 in this sequence, corresponding
to aa 252-613 of the wild-type sequence of ETA;)

SEQ ID NO: 3

```
  1 MQVQLQQSGPELKKPGETVKISCKASGYPFTNYGMNWVKQAPGQGLKWMG

51 WINTSTGESTFADDFKGRFDFSLETSANTAYLQINNLKSED[S]ATYFCARW

101 EVYHGYVPYWGQGTTVTVSSGGGGSGGGGSGGGGSDIQLTQSHKFLSTSV

151 GDRVSITCKASQDVYNAVAWYQQKPGQSPKLLIYSASSRYTGVPSRFTGS

201 GSGPDFTFTISSVQAEDLAVYFCQQHFRTPFTFGSGTKLEIKALEGGSLA

251 ALTAHQACHLPLETFTRHRQPRGWEQLEQCGYPVQRLVALYLAARLSWNQ

301 VDQVIRNALASPGSGGDLGEAIREQPEQARLALTLAAAESERFVRQGTGN

351 DEAGAASADVVSLTCPVAAGECAGPADSGDALLERNYPTGAEFLGDGGDV

401 SFSTRGTQWTVERLLQAHRQLEERGYVFVGYHGTFLEAAQSIVFGGVRA

451 RSQDLDAIWRGFYIAGDPALAYGYAQDQEPDARGRIRNGALLRVYVPRSS

501 LPGFYRTGLTLAAPEAAGEVERLIGHPLPLRLDAITGPEEEGGRLETILG

551 WPLAERTVVIPSAIPTDPRNVGGDLDPSSIPDKEQAISALPDYASQPGKP

601 PREDLK* 606
```

Nucleotide sequence encoding scFv(FRP5)-ETA (213)
[TCG] The nucleotides encoding the optimised amino acid
      position 92, here encoding the amino acid Serine is boxed

SEQ ID NO: 4

```
   1 ATGCAGGTACAACTGCAGCAGTCAGGACCTGAACTGAAGAAGCCTGGAGA

51 GACAGTCAAGATCTCCTGCAAGGCCTCTGGGTATCCTTTCACAAACTATG

101 GAATGAACTGGGTGAAGCAGGCTCCAGGACAGGGTTTAAAGTGGATGGGC

151 TGGATTAACACCTCCACTGGAGAGTCAACATTTGCTGATGACTTCAAGGG

201 ACGGTTTGACTTCTCTTTGGAAACCTCTGCCAACACTGCCTATTTGCAGA

251 TCAACAACCTCAAAAGTGAAGAC[TCG]GCTACATATTTCTGTGCAAGATGG

301 GAGGTTTACCACGGCTACGTTCCTTACTGGGGCCAAGGGACCACGGTCAC

351 CGTTTCCTCTGGCGGTGGCGGTTCTGGTGGCGGTGGCTCCGGCGGTGGCG

401 GTTCTGACATCCAGCTGACCCAGTCTCACAAATTCCTGTCCACTTCAGTA

451 GGAGACAGGGTCAGCATCACCTGCAAGGCCAGTCAGGATGTGTATAATGC

501 TGTTGCCTGGTATCAACAGAAACCAGGACAATCTCCTAAACTTCTGATTT

551 ACTCGGCATCCTCCCGGTACACTGGAGTCCCTTCTCGCTTCACTGGCAGT

601 GGCTCTGGGCCGGATTTCACTTTCACCATCAGCAGTGTGCAGGCTGAAGA

651 CCTGGCAGTTTATTTCTGTCAGCAACATTTTCGTACTCCATTCACGTTCG

701 GCTCGGGGACAAAATTGGAGATCAAAGCTCTAGAGGGCGGCAGCCTGGCC

751 GCGCTGACCGCGCACCAGGCCTGCCACCTGCCGCTGGAGACTTTCACCCG

801 TCATCGCCAGCCGCGCGGCTGGGAACAACTGGAGCAGTGCGGCTATCCGG

851 TGCAGCGGCTGGTCGCCCTCTACCTGGCGGCGCGACTGTCATGGAACCAG

901 GTCGACCAGGTGATCCGCAACGCCCTGGCCAGCCCCGGCAGCGGCGGCGA

951 CCTGGGCGAAGCGATCCGCGAGCAGCCGGAGCAGGCCCGTCTGGCCCTGA

1001 CCCTGGCCGCCGCCGAGAGCGAGCGCTTCGTCCGGCAGGGCACCGGCAAC
```

-continued

```
1051 GACGAGGCCGGCGCGGCCAGCGCCGACGTGGTGAGCCTGACCTGCCCGGT

1101 CGCCGCCGGTGAATGCGCGGGCCCGGCGGACAGCGGCGACGCCCTGCTGG

1151 AGCGCAACTATCCCACTGGCGCGGAGTTCCTCGGCGACGGTGGCGACGTC

1201 AGCTTCAGCACCCGCGGCACGCAGAACTGGACGGTGGAGCGGCTGCTCCA

1251 GGCGCACCGCCAACTGGAGGAGCGCGGCTATGTGTTCGTCGGCTACCACG

1301 GCACCTTCCTCGAAGCGGCGCAAAGCATCGTCTTCGGCGGGTGCGCGCG

1351 CGCAGCCAGGATCTCGACGCGATCTGGCGCGGTTTCTATATCGCCGGCGA

1401 TCCGGCGCTGGCCTACGGCTACGCCCAGGACCAGGAACCCGACGCGCGCG

1451 GCCGGATCCGCAACGGTGCCCTGCTGCGGGTCTATGTGCCGCGCTCGAGC

1501 CTGCCGGGCTTCTACCGCACCGGCCTGACCCTGGCCGCGCCGGAGGCGGC

1551 GGGCGAGGTCGAACGGCTGATCGGCCATCCGCTGCCGCTGCGCCTGGACG

1601 CCATCACCGGCCCCGAGGAGGAAGGCGGGCGCCTGGAGACCATTCTCGGC

1651 TGGCCGCTGGCCGAGCGCACCGTGGTGATTCCCTCGGCGATCCCCACCGA

1701 CCCGCGCAACGTCGGCGGCGACCTCGACCCGTCCAGCATCCCCGACAAGG

1751 AACAGGCGATCAGCGCCCTGCCGGACTACGCCAGCCAGCCCGGCAAACCG

1801 CCGCGCGAGGACCTGAAGTAA 1821
```

---

The invention claimed is:

1. An isolated polynucleotide encoding a polypeptide comprising a first amino acid sequence which comprises the amino acids 2-120 of SEQ ID NO:11 and a second amino acid sequence which comprises the amino acids 136-242 of SEQ ID NO:11, wherein said first amino acid sequence and said second amino acid sequence are linked by a peptide spacer group.

2. The isolated polynucleotide according to claim 1, wherein the first amino acid comprises the amino acids 1-120 of SEQ ID NO:11.

3. The isolated polynucleotide according to claim 1, wherein the first amino acid consists of the amino acids 1-120 of SEQ ID NO:11.

4. The isolated polynucleotide according to claim 1, wherein the first amino acid comprises the amino acids 2-120 of SEQ ID NO:1.

5. The isolated polynucleotide according to claim 1, wherein the first amino acid comprises the amino acids 1-120 of SEQ ID NO:1.

6. The isolated polynucleotide according to claim 1, wherein the first amino acid consists of the amino acids 1-120 of SEQ ID NO:1.

7. The isolated polynucleotide according to claim 1, wherein the second amino acid consists of the amino acids 136-242 of SEQ ID NO:11.

8. The isolated polynucleotide according to claim 1, wherein said polynucleotide encodes a polypeptide that comprises the amino acid sequence set forth in SEQ ID NO:11.

9. The isolated polynucleotide according to claim 1, wherein said polynucleotide encodes a polypeptide that consists of the amino acid sequence set forth in SEQ ID NO:11.

10. The isolated polynucleotide according to claim 1, wherein said polynucleotide encodes a polypeptide that comprises the amino acid sequence set forth in SEQ ID NO:1.

11. The isolated polynucleotide according to claim 1, wherein said polynucleotide encodes a polypeptide that consists of the amino acid sequence set forth in SEQ ID NO:1.

12. The isolated polynucleotide according to claim 1, wherein said polynucleotide encodes a polypeptide that comprises the amino acid sequence set forth in SEQ ID NO:3.

13. The isolated polynucleotide according to claim 1, wherein said polynucleotide encodes a polypeptide that consists of the amino acid sequence set forth in SEQ ID NO:3.

14. The isolated polynucleotide according to claim 1, wherein the polynucleotide comprises the nucleotide sequence set forth SEQ ID NO:2.

15. The isolated polynucleotide according to claim 1, wherein the polynucleotide consists of the nucleotide sequence set forth SEQ ID NO:2.

16. The isolated polynucleotide according to claim 1, wherein the polynucleotide comprises the nucleotide sequence set forth SEQ ID NO:4.

17. The isolated polynucleotide according to claim 1, wherein the polynucleotide consists of the nucleotide sequence set forth SEQ ID NO:4.

18. The isolated polynucleotide according to claim 1, wherein the peptide spacer group comprises 3 to 30 amino acids.

19. The isolated polynucleotide according to claim 1, wherein the peptide spacer group comprises 5 to 25 amino acids.

20. The isolated polynucleotide according to claim 1, wherein the peptide spacer group comprises 10 to 20 amino acids.

21. The isolated polynucleotide according to claim 18, wherein the peptide spacer group consists of amino acids selected from glycine and serine.

22. The isolated polynucleotide according to claim 18, wherein the peptide spacer group comprises repeating subunits of Gly-Gly-Gly-Gly-Ser (SEQ ID NO: 13).

23. The isolated polynucleotide according to claim 1, wherein the peptide spacer group comprises a 15 amino acid peptide consisting of three repeating subunits of Gly-Gly-Gly-Gly-Ser (SEQ ID NO: 13).

* * * * *

SEQUENCE LISTING

<160> NUMBER OF SEQ ID NOS: 13

<210> SEQ ID NO 1
<211> LENGTH: 242
<212> TYPE: PRT
<213> ORGANISM: artificial sequence
<220> FEATURE:
<223> OTHER INFORMATION: optimized scFv(FRP5) antibody fragment with M92S

<400> SEQUENCE: 1

```
Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Ser Ala Thr Tyr Phe
                85                  90                  95

Cys Ala Arg Trp Glu Val Tyr His Gly Tyr Val Pro Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Asp Ile Gln Leu Thr Gln Ser His Lys
    130                 135                 140

Phe Leu Ser Thr Ser Val Gly Asp Arg Val Ser Ile Thr Cys Lys Ala
145                 150                 155                 160
```

```
Ser Gln Asp Val Tyr Asn Ala Val Ala Trp Tyr Gln Lys Pro Gly
            165                 170                 175

Gln Ser Pro Lys Leu Leu Ile Tyr Ser Ala Ser Arg Tyr Thr Gly
            180                 185                 190

Val Pro Ser Arg Phe Thr Gly Ser Gly Ser Gly Pro Asp Phe Thr Phe
            195                 200                 205

Thr Ile Ser Ser Val Gln Ala Glu Asp Leu Ala Val Tyr Phe Cys Gln
            210                 215                 220

Gln His Phe Arg Thr Pro Phe Thr Phe Gly Ser Gly Thr Lys Leu Glu
225                 230                 235                 240

Ile Lys

<210> SEQ ID NO 2
<211> LENGTH: 726
<212> TYPE: DNA
<213> ORGANISM: artificial sequence
<220> FEATURE:
<223> OTHER INFORMATION: Coding sequence of optimized scFv(FRP5)
      antibody fragment

<400> SEQUENCE: 2
atgcaggtac aactgcagca gtcaggacct gaactgaaga agcctggaga cagtcaag        60 atctcctgca aggcctctgg gtatcctttc acaaactatg gaatgaactg ggtgaagcag     120
gctccaggac agggtttaaa gtggatgggc tggattaaca cctccactgg agagtcaaca     180
tttgctgatg acttcaaggg acggtttgac ttctcttttgg aaacctctgc aacactgcc    240 tatttgcaga tcaacaacct caaaagtgaa gactcggcta catatttctg tgcaagatgg     300
gaggtttacc acggctacgt tccttactgg ggccaaggga ccacggtcac cgtttcctct    360
ggcggtggcg gttctggtgg cggtggctcc ggcggtggcg gttctgacat ccagctgacc    420
cagtctcaca attcctgtc cacttcagta ggagacaggg tcagcatcac ctgcaaggcc    480
agtcaggatg tgtataatgc tgttgcctgg tatcaacaga aaccaggaca atctcctaaa     540
cttctgattt actcggcatc ctcccggtac actggagtcc cttctcgctt cactggcagt     600
ggctctgggc cggatttcac tttcaccatc agcagtgtgc aggctgaaga cctggcagtt     660
tatttctgtc agcaacattt tcgtactcca ttcacgttcg gctcggggac aaaattggag     720
atcaaa                                                                 726

<210> SEQ ID NO 3
<211> LENGTH: 606
<212> TYPE: PRT
<213> ORGANISM: artificial sequence
<220> FEATURE:
<223> OTHER INFORMATION: scFv(FRP5)-ETA (213)

<400> SEQUENCE: 3

Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Ser Ala Thr Tyr Phe
```

```
                  85                  90                  95
Cys Ala Arg Trp Glu Val Tyr His Gly Tyr Val Pro Tyr Trp Gly Gln
                100                 105                 110

Gly Thr Thr Val Thr Val Ser Ser Gly Gly Gly Ser Gly Gly Gly
                115                 120                 125

Gly Ser Gly Gly Gly Ser Asp Ile Gln Leu Thr Gln Ser His Lys
                130                 135                 140

Phe Leu Ser Thr Ser Val Gly Asp Arg Val Ser Ile Thr Cys Lys Ala
145                 150                 155                 160

Ser Gln Asp Val Tyr Asn Ala Val Ala Trp Tyr Gln Gln Lys Pro Gly
                165                 170                 175

Gln Ser Pro Lys Leu Leu Ile Tyr Ser Ala Ser Ser Arg Tyr Thr Gly
                180                 185                 190

Val Pro Ser Arg Phe Thr Gly Ser Gly Ser Gly Pro Asp Phe Thr Phe
                195                 200                 205

Thr Ile Ser Ser Val Gln Ala Glu Asp Leu Ala Val Tyr Phe Cys Gln
                210                 215                 220

Gln His Phe Arg Thr Pro Phe Thr Phe Gly Ser Gly Thr Lys Leu Glu
225                 230                 235                 240

Ile Lys Ala Leu Glu Gly Gly Ser Leu Ala Ala Leu Thr Ala His Gln
                245                 250                 255

Ala Cys His Leu Pro Leu Glu Thr Phe Thr Arg His Arg Gln Pro Arg
                260                 265                 270

Gly Trp Glu Gln Leu Glu Gln Cys Gly Tyr Pro Val Gln Arg Leu Val
                275                 280                 285

Ala Leu Tyr Leu Ala Ala Arg Leu Ser Trp Asn Gln Val Asp Gln Val
                290                 295                 300

Ile Arg Asn Ala Leu Ala Ser Pro Gly Ser Gly Gly Asp Leu Gly Glu
305                 310                 315                 320

Ala Ile Arg Glu Gln Pro Glu Gln Ala Arg Leu Ala Leu Thr Leu Ala
                325                 330                 335

Ala Ala Glu Ser Glu Arg Phe Val Arg Gln Gly Thr Gly Asn Asp Glu
                340                 345                 350

Ala Gly Ala Ala Ser Ala Asp Val Val Ser Leu Thr Cys Pro Val Ala
                355                 360                 365

Ala Gly Glu Cys Ala Gly Pro Ala Asp Ser Gly Asp Ala Leu Leu Glu
                370                 375                 380

Arg Asn Tyr Pro Thr Gly Ala Glu Phe Leu Gly Asp Gly Gly Asp Val
385                 390                 395                 400

Ser Phe Ser Thr Arg Gly Thr Gln Asn Trp Thr Val Glu Arg Leu Leu
                405                 410                 415

Gln Ala His Arg Gln Leu Glu Glu Arg Gly Tyr Val Phe Val Gly Tyr
                420                 425                 430

His Gly Thr Phe Leu Glu Ala Ala Gln Ser Ile Val Phe Gly Gly Val
                435                 440                 445

Arg Ala Arg Ser Gln Asp Leu Asp Ala Ile Trp Arg Gly Phe Tyr Ile
450                 455                 460

Ala Gly Asp Pro Ala Leu Ala Tyr Gly Tyr Ala Gln Asp Gln Glu Pro
465                 470                 475                 480

Asp Ala Arg Gly Arg Ile Arg Asn Gly Ala Leu Leu Arg Val Tyr Val
                485                 490                 495

Pro Arg Ser Ser Leu Pro Gly Phe Tyr Arg Thr Gly Leu Thr Leu Ala
                500                 505                 510
```

-continued

```
        Ala Pro Glu Ala Ala Gly Glu Val Glu Arg Leu Ile Gly His Pro Leu
            515                 520                 525
        Pro Leu Arg Leu Asp Ala Ile Thr Gly Pro Glu Glu Gly Gly Arg
            530                 535                 540
        Leu Glu Thr Ile Leu Gly Trp Pro Leu Ala Glu Arg Thr Val Val Ile
        545                 550                 555                 560
        Pro Ser Ala Ile Pro Thr Asp Pro Arg Asn Val Gly Gly Asp Leu Asp
                        565                 570                 575
        Pro Ser Ser Ile Pro Asp Lys Glu Gln Ala Ile Ser Ala Leu Pro Asp
                        580                 585                 590
        Tyr Ala Ser Gln Pro Gly Lys Pro Pro Arg Glu Asp Leu Lys
                        595                 600                 605
```

<210> SEQ ID NO 4
<211> LENGTH: 1821
<212> TYPE: DNA
<213> ORGANISM: artificial sequence
<220> FEATURE:
<223> OTHER INFORMATION: coding sequence of scFv(FRP5)-ETA (213)

<400> SEQUENCE: 4

| | | |
|---|---|---|
| atgcaggtac aactgcagca gtcaggacct gaactgaaga agcctggaga cagtcaag | 60 |
| atctcctgca aggcctctgg gtatcctttc acaaactatg gaatgaactg ggtgaagcag | 120 |
| gctccaggac agggtttaaa gtggatgggc tggattaaca cctccactgg agagtcaaca | 180 |
| tttgctgatg acttcaaggg acggtttgac ttctcttttgg aaacctctgc caacactgcc | 240 |
| tatttgcaga tcaacaacct caaaagtgaa gactcggcta catatttctg tgcaagatgg | 300 |
| gaggtttacc acggctacgt tccttactgg ggccaaggga ccacggtcac cgtttcctct | 360 |
| ggcggtggcg gttctggtgg cggtggctcc ggcggtggcg gttctgacat ccagctgacc | 420 |
| cagtctcaca aattcctgtc cacttcagta ggagacaggg tcagcatcac ctgcaaggcc | 480 |
| agtcaggatg tgtataatgc tgttgcctgg tatcaacaga aaccaggaca atctcctaaa | 540 |
| cttctgattt actcggcatc ctcccggtac actggagtcc cttctcgctt cactggcagt | 600 |
| ggctctgggc cggatttcac tttcaccatc agcagtgtgc aggctgaaga cctggcagtt | 660 |
| tatttctgtc agcaacattt tcgtactcca ttcacgttcg gctcggggac aaaattggag | 720 |
| atcaaagctc tagagggcgg cagcctggcc gcgctgaccg cgcaccaggc ctgccacctg | 780 |
| ccgctggaga cttttcacccg tcatcgccag ccgcgcggct gggaacaact ggagcagtgc | 840 |
| ggctatccgg tgcagcggct ggtcgccctc tacctggcgg cgcgactgtc atggaaccag | 900 |
| gtcgaccagg tgatccgcaa cgccctggcc agccccggca gcggcggcga cctgggcgaa | 960 |
| gcgatccgcg agcagccgga gcaggcccgt ctggccctga cctggccgcc gccgagagc | 1020 |
| gagcgcttcg tccggcaggg caccggcaac gacgaggccg gcgcggccag cgccgacgtg | 1080 |
| gtgagcctga cctgccggt cgccgccggt gaatgcgcgg gccgggcgga cagcggcgac | 1140 |
| gccctgctgg agcgcaacta tcccactggc gcggagttcc tcggcgacgg tggcgacgtc | 1200 |
| agcttcagca cccgcggcac gcagaactgg acggtggagc ggctgctcca ggcgcaccgc | 1260 |
| caactggagg agcgcggcta tgtgttcgtc ggctaccacg gcaccttcct cgaagcggcg | 1320 |
| caaagcatcg tcttcggcgg ggtgcgcgcg cgcagccagg atctcgacgc gatctggcgc | 1380 |
| ggtttctata tcgccggcga tccggcgctg gcctacggct acgcccagga ccaggaaccc | 1440 |
| gacgcgcgcg gccggatccg caacggtgcc ctgctgcggg tctatgtgcc gcgctcgagc | 1500 |
| ctgccgggct tctaccgcac cggcctgacc ctggccgcgc cggaggcggc gggcgaggtc | 1560 |

```
gaacggctga tcggccatcc gctgccgctg cgcctggacg ccatcaccgg ccccgaggag    1620
gaaggcgggc gcctggagac cattctcggc tggccgctgg ccgagcgcac cgtggtgatt    1680
ccctcggcga tccccaccga cccgcgcaac gtcggcggcg acctcgaccc gtccagcatc    1740
cccgacaagg aacaggcgat cagcgccctg ccggactacg ccagccagcc cggcaaaccg    1800
ccgcgcgagg acctgaagta a                                              1821
```

<210> SEQ ID NO 5
<211> LENGTH: 39
<212> TYPE: DNA
<213> ORGANISM: artificial sequence
<220> FEATURE:
<223> OTHER INFORMATION: primer 5'NdeI-scFv(FRP5)

<400> SEQUENCE: 5

```
cgattagcat atgcaggtac aactgcagca gtcaggacc                             39
```

<210> SEQ ID NO 6
<211> LENGTH: 27
<212> TYPE: DNA
<213> ORGANISM: artificial sequence
<220> FEATURE:
<223> OTHER INFORMATION: primer 3'XbaI-scFv(FRP5)

<400> SEQUENCE: 6

```
gctgccgccc tctagagctt tgatctc                                          27
```

<210> SEQ ID NO 7
<211> LENGTH: 36
<212> TYPE: DNA
<213> ORGANISM: artificial sequence
<220> FEATURE:
<223> OTHER INFORMATION: primer pSES212_M92S_sense

<400> SEQUENCE: 7

```
cctcaaaagt gaagactcgg ctacatattt ctgtgc                                36
```

<210> SEQ ID NO 8
<211> LENGTH: 36
<212> TYPE: DNA
<213> ORGANISM: artificial sequence
<220> FEATURE:
<223> OTHER INFORMATION: primer pSES212_M92S_as

<400> SEQUENCE: 8

```
gcacagaaat atgtagccga gtcttcactt ttgagg                                36
```

<210> SEQ ID NO 9
<211> LENGTH: 99
<212> TYPE: PRT
<213> ORGANISM: artificial sequence
<220> FEATURE:
<223> OTHER INFORMATION: N-terminal amino acid sequence of scFv(FRP5)
      having Met at 92

<400> SEQUENCE: 9

```
Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60
```

```
Phe Lys Gly Arg Phe Asp Phe Ser Leu Glu Thr Ser Ala Asn Thr Ala
 65                  70                  75                  80

Tyr Leu Gln Ile Asn Asn Leu Lys Ser Glu Asp Met Ala Thr Tyr Phe
                 85                  90                  95

Cys Ala Arg

<210> SEQ ID NO 10
<211> LENGTH: 297
<212> TYPE: DNA
<213> ORGANISM: artificial sequence
<220> FEATURE:
<223> OTHER INFORMATION: DNA encoding SEQ ID NO:9

<400> SEQUENCE: 10
atgcaggtac aactgcagca gtcaggacct gaactgaaga agcctggaga cagtcaag       60 atctcctgca aggcctctgg gtatccttc acaaactatg gaatgaactg ggtgaagcag     120
gctccaggac agggtttaaa gtggatgggc tggattaaca cctccactgg agagtcaaca   180
tttgctgatg acttcaaggg acggtttgac ttctctttgg aaacctctgc caacactgcc    240
tatttgcaga tcaacaacct caaaagtgaa gacatggcta catatttctg tgcaaga         297

<210> SEQ ID NO 11
<211> LENGTH: 242
<212> TYPE: PRT
<213> ORGANISM: artificial sequence
<220> FEATURE:
<223> OTHER INFORMATION: scFv(FRP5) antibody fragment
<220> FEATURE:
<221> NAME/KEY: MISC_FEATURE
<222> LOCATION: (92)..(92)
<223> OTHER INFORMATION: Xaa can be any naturally occurring amino acid
      or any non-naturally occurring amino acid or any modified amino
      acid or be absent, with the proviso that Xaa is not methionine

<400> SEQUENCE: 11

Met Gln Val Gln Leu Gln Gln Ser Gly Pro Glu Leu Lys Lys Pro Gly
  1               5                  10                  15

Glu Thr Val Lys Ile Ser Cys Lys Ala Ser Gly Tyr Pro Phe Thr Asn
                 20                  25                  30

Tyr Gly Met Asn Trp Val Lys Gln Ala Pro Gly Gln Gly Leu Lys Trp
             35                  40                  45

Met Gly Trp Ile Asn Thr Ser Thr Gly Glu Ser Thr Phe Ala Asp Asp
 50                  55                  60

Phe Lys Gly Arg Phe Asp Phe Ser Leu Glu Thr Ser Ala Asn Thr Ala
 65                  70                  75                  80

Tyr Leu Gln Ile Asn Asn Leu Lys Ser Glu Asp Xaa Ala Thr Tyr Phe
                 85                  90                  95

Cys Ala Arg Trp Glu Val Tyr His Gly Tyr Val Pro Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Gly Ser Asp Ile Gln Leu Thr Gln Ser His Lys
        130                 135                 140

Phe Leu Ser Thr Ser Val Gly Asp Arg Val Ser Ile Thr Cys Lys Ala
145                 150                 155                 160

Ser Gln Asp Val Tyr Asn Ala Val Ala Trp Tyr Gln Gln Lys Pro Gly
                165                 170                 175

Gln Ser Pro Lys Leu Leu Ile Tyr Ser Ala Ser Ser Arg Tyr Thr Gly
            180                 185                 190
```

```
Val Pro Ser Arg Phe Thr Gly Ser Gly Ser Gly Pro Asp Phe Thr Phe
            195                 200                 205

Thr Ile Ser Ser Val Gln Ala Glu Asp Leu Ala Val Tyr Phe Cys Gln
        210                 215                 220

Gln His Phe Arg Thr Pro Phe Thr Phe Gly Ser Gly Thr Lys Leu Glu
225                 230                 235                 240

Ile Lys

<210> SEQ ID NO 12
<211> LENGTH: 241
<212> TYPE: PRT
<213> ORGANISM: artificial sequence
<220> FEATURE:
<223> OTHER INFORMATION: scFv(FRP5) antibody fragment wherein M92 was
      deleted

<400> SEQUENCE: 12

Met Gln Val Gln Leu Gln Gln Ser Gly Pro Glu Leu Lys Lys Pro Gly
1               5                   10                  15

Glu Thr Val Lys Ile Ser Cys Lys Ala Ser Gly Tyr Pro Phe Thr Asn
            20                  25                  30

Tyr Gly Met Asn Trp Val Lys Gln Ala Pro Gly Gln Gly Leu Lys Trp
        35                  40                  45

Met Gly Trp Ile Asn Thr Ser Thr Gly Glu Ser Thr Phe Ala Asp Asp
    50                  55                  60

Phe Lys Gly Arg Phe Asp Phe Ser Leu Glu Thr Ser Ala Asn Thr Ala
65                  70                  75                  80

Tyr Leu Gln Ile Asn Asn Leu Lys Ser Glu Asp Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Leu Thr Gln Ser His Lys Phe
    130                 135                 140

Leu Ser Thr Ser Val Gly Asp Arg Val Ser Ile Thr Cys Lys Ala Ser
145                 150                 155                 160

Gln Asp Val Tyr Asn Ala Val Ala Trp Tyr Gln Lys Pro Gly Gln
                165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
        195                 200                 205

Ile Ser Ser Val Gln Ala Glu Asp Leu Ala Val Tyr Phe Cys Gln Gln
    210                 215                 220

His Phe Arg Thr Pro Phe Thr Phe Gly Ser Gly Thr Lys Leu Glu Ile
225                 230                 235                 240

Lys

<210> SEQ ID NO 13
<211> LENGTH: 5
<212> TYPE: PRT
<213> ORGANISM: artificial sequence
<220> FEATURE:
<223> OTHER INFORMATION: peptide spacer subunit
```

-continued

```
<400> SEQUENCE: 13

Gly Gly Gly Gly Ser
1               5
```